United States Patent [19]  
Sato et al.

[11] Patent Number: 5,030,776  
[45] Date of Patent: Jul. 9, 1991

[54] PROCESS FOR PRODUCING NITROBENZENES

[75] Inventors: Hiroshi Sato; Koichi Nagai; Hiroshi Yoshioka; Yoshihiko Nagaoka, all of Ehime, Japan

[73] Assignee: Sumitomo Chemical Co., Ltd., Osaka, Japan

[21] Appl. No.: 533,823

[22] Filed: Jun. 6, 1990

[30] Foreign Application Priority Data

Jun. 8, 1989 [JP] Japan ................... 1-147614

[51] Int. Cl.$^5$ ........................... C07C 205/11
[52] U.S. Cl. ................... 568/940; 568/937; 568/939
[58] Field of Search ............ 568/937, 939, 940

[56] References Cited

U.S. PATENT DOCUMENTS

| 2,008,045 | 7/1935 | Simon | 568/939 |
|---|---|---|---|
| 2,109,873 | 3/1938 | Wilhelm | 568/932 |
| 3,966,830 | 6/2976 | Shimada et al. | 260/646 |
| 4,107,220 | 8/1978 | Owsley et al. | 568/937 |
| 4,112,006 | 9/1978 | Schubert et al. | 260/645 |
| 4,347,389 | 8/1982 | Schumacher et al. | 568/937 |
| 4,415,744 | 11/1983 | Schumacher et al. | 560/20 X |
| 4,551,568 | 11/1985 | Sato et al. | 568/939 |
| 4,600,702 | 7/1986 | Schumacher | 502/200 X |
| 4,618,733 | 10/1986 | Schumacher | 568/927 |
| 4,628,131 | 12/1986 | Schumacher | 568/937 |
| 4,754,083 | 6/1988 | Reith et al. | 568/932 |

FOREIGN PATENT DOCUMENTS 51-063134  6/1976  Japan .  
1213256   2/1988  Japan ................... 568/939

Primary Examiner—Robert L. Stoll  
Assistant Examiner—Chhaya Sayala  
Attorney, Agent, or Firm—Cushman, Darby & Cushman

[57] ABSTRACT

Nitrobenzenes are prepared by nitrating benzenes in vapor phase using nitric acid as a nitrating agent and under continuous or intermittent feeding of sulfuric acid as a catalyst in the presence of a catalyst comprising sulfuric acid supported on a carrier or in the presence of only a carrier. This process can provide very high and prolonged nitration activity.

10 Claims, No Drawings

PROCESS FOR PRODUCING NITROBENZENES

The present invention relates to a process for producing nitrobenzenes and more particularly to a process for producing nitrobenzenes by nitration of benzenes in a vapor phase using nitric acid as a nitrating agent and sulfuric acid as a catalyst.

Nitrobenzenes are important key industrial chemicals used as raw materials for dyes, medicines, agricultural chemicals, and the like.

One of economical production processes which is still popular is that proposed by E. Mitsherlich in 1834, namely, nitrating benzenes in a liquid phase with a mixture of concentrated nitric acid and concentrated sulfuric acid. This process requires so large amount of sulfuric acid that large quantities of waste sulfuric acid and waste water are incidentally produced. This is a severe problem from an industrial point of view. In order to solve the problem, a process is proposed where aromatic sulfonic acids supported on carriers are used in place of the concentrated sulfuric acid. (Japanese Patent Kokai Nos. 48-18239, 49-18833 and 50-4030). However, the processes which are effected in a liquid phase still suffers from the problems that a large amount of catalyst is needed and that water by-produced causes deactivation of the catalyst. Accordingly, concentrated nitric acid of at least 90% or fuming nitric acid has to be used for the nitration, and furthermore the catalyst has to be subjected to azeotropic dehydration for reuse.

Another approach is nitration effected in a vapor phase. That is, the nitration is conducted with nitric acid in the presence of a catalyst comprising an inorganic acid such as sulfuric acid or phosphoric acid supported on carriers (Japanese Patent Kokai Nos. 50-126626, 50-126627, 51-63134 and 53-12823). However, these processes also have problems, i.e., insufficiency in catalytic activity and short life of catalysts.

The inventors have made intensive research in an attempt to find a process for production of nitrobenzenes in a vapor phase using nitric acid as a nitrating agent. As a result, it has been found that reduction in activity of catalysts comprising sulfuric acid supported on carriers is caused due to elimination of sulfuric acid from the carriers, that the reduction of catalytic activity does not occur at all if sulfuric acid is replenished in an amount corresponding to that of the sulfuric acid which has eliminated from the carrier and that extremely high nitration activity can also be maintained by continuously or intermittently feeding a catalytic amount, namely, a slight amount of sulfuric acid in the presence of only the carriers.

According to the present invention, a process for producing nitrobenzenes by nitration of benzenes in vapor phase using nitric acid as a nitrating agent, is provided, wherein the nitration is carried out while sulfuric acid is continuously or intermittently fed as a catalyst in the presence of carriers for the sulfuric acid.

The present invention will be explained in detail below.

As the carriers used in the present invention, mention may be made of, for example, silica carriers such as silica gel, diatomaceous earth, silica sand, and silica wool and inorganic compounds such as silicon carbide, silica-alumina, zeolite, titania, zirconia, alumina, active carbon, and graphite. Silica carriers such as silica gel, especially, dried silica sol, diatomaceous earth, silica sand and silica wool and silicon carbide are preferred, taking into consideration of their nitration activity and force for inhibiting sulfuric acid from being eliminated from the catalysts or retention of sulfuric acid.

The carriers desirably have sulfuric acid supported thereon, since an induction period before the reaction begins to start is shortened.

Amount of sulfuric acid to be fed as a catalyst is usually about 1/10–1/50,000, preferably about 1/100–1/50,000, more preferably about 1/500–1/10,000 on the basis of the weight of nitric acid. Sulfuric acid as the catalyst is fed continuously or intermittently. Sulfuric acid may be fed alone or as a mixture with any of the starting materials. For example, a catalytic amount of the sulfuric acid is dissolved in the nitric acid before it is fed.

In the case of feeding sulfuric acid intermittently, for example, a given amount of sulfuric acid is fed alone or in the form of a mixture with any other starting materials once a day. Since catalyst activity and retention of sulfuric acid vary depending on varieties of carriers, frequency of feeding sulfuric acid and an amount per feed vary depending on carriers used. These factors are determined on the basis of a change in catalytic activity during the reaction within the range of an amount of sulfuric acid against an amount of nitric acid mentioned above.

Concentration of nitric acid as the nitrating agent is not critical. Concentrated nitric acid and diluted nitric acid may be used. One of the advantages of the present invention to the conventional processes is that dilute nitric acid is usable and this brings about advantage not only in cost, but in materials of reaction instruments.

Benzenes which are one of the starting materials include, for example, benzene, chlorobenzene and toluene.

Nitration in a vapor phase is carried out by feeding vapor of the starting benzenes and vapor of the nitric acid over catalysts. The vapors may be diluted with an inert gas such as nitrogen, helium, argon, carbon dioxide or air.

Molar ratio of the nitric acid to the benzenes is usually about 5/1–1/10, preferably about 2/1–1/5, and reaction temperature is usually about 100°–300° C., preferably about 120°–200° C. Conditions for feeding of the starting materials (W/F) are not critical, but usually are selected within the range of about 0.1–100 g-catalyst h/mol.

The present reaction is carried out in conventional apparatuses for vapor phase flow reaction of fixed bed or fluidized bed. The reaction product is washed with alkali and then recovered by distillation.

According to the present invention, since nitration activity can be maintained by the sulfuric acid fed, substantially no deterioration of the activity occurs and nitrobenzenes are produced selectively in high yield for a long period of time. In addition, the fact that dilute nitric acid is usable as a nitrating agent makes to increase economical value of the process of the present invention.

The following nonlimiting examples explain the present invention in more detail.

REFERENCE EXAMPLE 1

A mixture of aqueous silica sol (300 ml, SNOWTEX N; $SiO_2$=20% manufactured by Nissan Chemical Industries, Ltd.) and 97% sulfuric acid (3.6 ml) was vacuum dried at 120° C. for 3 hours by a rotary evaporator to prepare a catalyst comprising 10% of sulfuric acid supported on silica gel. This is referred to as catalyst No. 1.

REFERENCE EXAMPLE 2

A mixture each of carriers (20 g each) shown in Table 1 and 97% sulfuric acid (1.2 ml each) was vacuum dried at 120° C. for 3 hours using a rotary evaporator to prepare a catalyst each comprising 10% of sulfuric acid supported on the carrier. The resulting catalysts are referred to as catalyst Nos. 2-9.

TABLE 1

| Catalyst No. | Carrier |
|---|---|
| 2 | Diatomaceous earth |
| 3 | Silica sand |
| 4 | Silica wool |
| 5 | Silicon carbide |
| 6 | Titania |
| 7 | Zirconia |
| 8 | Y-alumina |
| 9 | α-alumina |

EXAMPLE 1

Nitration of benzene with dilute nitric acid (70%) in a vapor phase was effected using silicon carbide (35 ml) as a carrier. Dilute nitric acid in which sulfuric acid in an amount of 1/100 (weight ratio based on the nitric acid) was dissolved was fed as a catalyst. Reaction was carried out in an apparatus for a vapor phase flow reaction of fixed bed made of pyrex. Nitrogen gas was used as a carrier gas. Reaction conditions were as follows.

Feed composition (mmol/h);
Benzene/$HNO_3$/$H_2O$/$N_2$/$H_2SO_4$ = 40/20/30/110/0.128
Total feed = 200 mmol/h
∴ W/F = 175 (ml-carrier·h/total feed mol)
∴ SV (space velocity) = 128 ml/ml·h
Reaction temperature (furnace temperature) = 140° C.

The product was trapped at 0° C. and then the trapped solution was analyzed by liquid chromatography and gas composition of a vapor phase portion was analyzed by gas chromatography. Unaltered nitric acid was obtained by alkalimetry of the trapped solution and conversion of nitric acid was calculated. Time and the results of reaction are shown in Table 2. The results of reaction are shown based on nitric acid.

TABLE 2

| Time (days) | Conversion of $HNO_3$ (%) | Yield of NB[1] (%) | Selectivity for NB (%) | STY of NB[2] (%) |
|---|---|---|---|---|
| 2 | 96.3 | 94.3 | 97.9 | 0.067 |
| 10 | 98.4 | 94.6 | 96.2 | 0.067 |
| 60 | 98.0 | 95.6 | 97.6 | 0.068 |

[1]NB: Nitrobenzene
[2]STY: Space time yield (Kg — NB/1 — carrier · h)

EXAMPLE 2

Nitration of benzene was carried out in the same manner as in Example 1 except that an amount of silicon carbide as a carrier was 3 g in palce of the 35 ml and an amount of sulfuric acid fed was 1/1000 in place of the 100 (weight ratio on the basis of the weight of nitric acid). Reaction conditions were as follows.

Feed composition (mmol/h);
Benzene/$HNO_3$/$H_2O$/$N_2$/$H_2SO_4$ = 40/20/30/110/0.0128
Total feed = 200 mmol/h
∴ W/F = 1500 (ml-carrier·h/total feed mol)
∴ SV (space velocity) = 1500 (1/h)
Reaction temperature (furnace temperature) = 140° C.

Time and the results of reaction are shown in Table 3. The results of reaction are shown based on nitric acid.

TABLE 3

| Time (days) | Conversion of $HNO_3$ (%) | Yield of NB[1] (%) | Selectivity for NB (%) | STY of NB[2] (%) |
|---|---|---|---|---|
| 1 | 21.8 | 21.7 | 99.7 | 0.18 |
| 2 | 88.5 | 87.3 | 98.7 | 0.72 |
| 3 | 96.3 | 94.6 | 98.3 | 0.77 |
| 10 | 96.8 | 96.4 | 99.6 | 0.79 |
| 60 | 96.0 | 93.0 | 96.9 | 0.76 |

[1]NB: Nitrobenzene
[2]STY: Space time yield (Kg — NB/1 — carrier · h)

EXAMPLE 3

Nitration of benzene with 70% dilute nitric acid was carried out in the same manner as in Example 1 using the catalyst prepared in Reference Example 1 which comprised 10% of sulfuric acid supported on silica in place of the silicon carbide. An amount of sulfuric acid fed was 1/1000 in palce of the 1/100 (weight ratio on the basis of the weight of nitric acid). Time and the results of the reaction are shown in Table 4. The results are shown based on nitric acid.

TABLE 4

| Time (days) | Conversion of $HNO_3$ (%) | Yield of NB[1] (%) | Selectivity for NB (%) | STY of NB[2] (%) |
|---|---|---|---|---|
| 1 | 96.9 | 94.3 | 97.4 | 0.77 |
| 5 | 96.5 | 92.8 | 96.1 | 0.76 |
| 10 | 96.1 | 92.3 | 96.0 | 0.76 |
| 60 | 96.2 | 92.6 | 96.2 | 0.76 |

[1]NB: Nitrobenzene
[2]STY: Space time yield (Kg — NB/1 — carrier · h)

EXAMPLE 4

Nitration was effected in the same manner as in Example 3 except that an amount of sulfuric acid fed was 1/5000 in place of the 1/1000 (weight ratio on the basis of nitric acid). Time and the results of the reaction are shown in Table 5. The results are shown based on nitric acid.

TABLE 5

| Time (days) | Conversion of $HNO_3$ (%) | Yield of NB[1] (%) | Selectivity for NB (%) | STY of NB[2] (%) |
|---|---|---|---|---|
| 1 | 97.1 | 94.1 | 97.0 | 0.77 |
| 5 | 96.1 | 94.3 | 98.1 | 0.77 |
| 10 | 96.5 | 93.8 | 97.2 | 0.77 |
| 60 | 96.2 | 92.9 | 96.6 | 0.76 |

[1]NB: Nitrobenzene
[2]STY: Space time yield (Kg — NB/1 — carrier · h)

EXAMPLE 5

Nitration was effected in the same manner as in Example 3 using catalysts comprising 10% of sulfuric acid supported on various supports which were prepared in Reference Example 2 (Table 1). An amount of sulfuric acid fed was 1/1000 (weight ratio on the basis of nitric acid). Time and the results of the reaction are shown in Table 6. The results are shown based on nitric acid.

TABLE 6

| Run No. | Catalyst No. | Time (days) | Conversion of HNO$_3$ (%) | Yield of NB[*1] (%) | Selectivity for NB (%) |
|---|---|---|---|---|---|
| 1 | 2 | 1 | 97.5 | 96.0 | 98.5 |
|   |   | 10 | 97.0 | 95.2 | 98.1 |
| 2 | 3 | 1 | 97.1 | 94.4 | 97.3 |
|   |   | 10 | 96.7 | 94.7 | 98.0 |
| 3 | 4 | 1 | 97.4 | 96.1 | 98.6 |
|   |   | 10 | 95.3 | 93.6 | 98.2 |
| 4 | 5 | 1 | 97.5 | 95.6 | 98.0 |
|   |   | 10 | 97.4 | 95.1 | 97.6 |
| 5 | 6 | 1 | 92.0 | 90.0 | 97.8 |
|   |   | 10 | 83.8 | 81.5 | 97.3 |
| 6 | 7 | 1 | 95.1 | 92.0 | 96.7 |
|   |   | 10 | 84.4 | 82.5 | 97.8 |
| 7 | 8 | 1 | 42.2 | 40.7 | 96.4 |
|   |   | 10 | 43.9 | 42.7 | 97.2 |
| 8 | 9 | 1 | 34.0 | 33.2 | 97.7 |
|   |   | 10 | 22.9 | 22.2 | 97.0 |

[*1] NB: Nitrobenzene

COMPARATIVE EXAMPLE 1

Nitration of benzene was effected in the same manner as in Example 5 using catalyst No. 2 (10% of sulfuric acid supported on diatomaceous earth) feeding no sulfuric acid. Results are shown in Table 7.

TABLE 7

| Time (days) | Conversion of HNO$_3$ (%) | Yield of NB[*1] (%) | Selectivity for NB (%) |
|---|---|---|---|
| 1 | 97.5 | 96.0 | 98.5 |
| 3 | 57.3 | 56.1 | 98.0 |
| 5 | 0 | 0 | — |

[*1] NB: Nitrobenzene

EXAMPLE 6

Nitration of chlorobenzene in a vapor phase was effected in the same manner as in Example 3 using the catalyst No. 1 (10% of sulfuric acid supported on silica) and using chlorobenzene in place of the benzene. Reaction temperature was 160° C. in place of 140° C. The results are shown in Table 8 based on nitric acid.

TABLE 8

| Time (days) | Conversion of HNO$_3$ (%) | Yield of CNB[*1] (%) | Selectivity for CNB (%) | P/O ratio of CNB[*2] |
|---|---|---|---|---|
| 1 | 93.5 | 87.0 | 93.0 | 2.2 |
| 10 | 93.1 | 86.8 | 93.2 | 2.2 |

[*1] CNB: Chloronitrobenzene
[*2] P(para)/O(ortho) ratio of CNB isomers.

EXAMPLE 7

Nitration of toluene in a vapor phase was effected in the same manner as in Example 3 using the catalyst No. 1 (10% of sulfuric acid supported on silica) and using toluene in place of the benzene. Reaction temperature was 140° C. The results are shown in Table 9 based on nitric acid.

TABLE 9

| Time (days) | Conversion of HNO$_3$ (%) | Yield of NT[*1] (%) | Selectivity of NT (%) | P/O ratio of NT[*2] |
|---|---|---|---|---|
| 1 | 98.5 | 53.1 | 54.0 | 0.95 |
| 10 | 97.2 | 53.3 | 54.8 | 0.95 |

[*1] NT: Nitrotoluene
[*2] P(para)/O(ortho) ratio of NT isomers

We claim:

1. A process for producing nirobenzenes which comprises
    nitrating benzenes in a vapor phase with nitric acid in the presence of a carrier for sulfuric acid as a catalyst; and feeding continuously or intermittently sulfuric acid during the nitration.
2. A process according to claim 1 wherein the benzenes are benzene, chlorobenzene or toluene.
3. A process according to claim 1, wherein the carrier is silica gel, diatomaceous earth, silica sand, silica wool, silicon carbide, silica-alumina, zeolite, titania, zirconia, alumina, active carbon or graphite.
4. A process according to claim 1, wherein the carrier is silica gel, diatomaceous earth, silica sand, silica wool or silicon carbide.
5. A process according to claim 1, wherein feeding amount of sulfuric acid is 1/10-1/50,000 by weight on the basis of nitric acid.
6. A process according to claim 1, wherein molar ratio of nitric acid and benzenes is 5/1-1/10.
7. A process according to claim 1, wherein the reaction is carried out at 100°-300° C.
8. A process according to claim 1, wherein the condition for feeding starting material is 0.1-100 g-cat. h/mol.
9. A process for producing nitrobenzenes which comprises
    nitrating benzene in a vapor phase with nitric acid in the presence of sulfuric acid wherein the nitration is carried out while continuously or intermittently feeding sulfuric acid in the presence of a carrier for the sulfuric acid, and wherein said carrier supports sulfuric acid before the nitration.
10. A process for producing nitrobenzenes comprising nitrating aromatics selected from the group consisting of benzene, chlorobenzene and toluene at 100°-300° C., in the vapor phase, with nitric acid in the presence of a carrier for sulfuric acid, which carrier is selected from the group consisting of silica gel, diatomaceous earth, silica sand, silica wool, silica carbide, silica-alumina, zeolite, titania, zirconia, alumina, active carbon and graphite, and introducing continously or intermittently sulfuric acid during the nitration, wherein the molar ratio of nitric acid and aromatics is 5/1-1/10.

* * * * *